United States Patent [19]

Langer

[11] Patent Number: 4,895,965

[45] Date of Patent: Jan. 23, 1990

[54] METHOD FOR MAKING CARBOXY ARYL TERMINATED ORGANOSILOXANES

[75] Inventor: Matthew E. Langer, Guilderland, N.Y.

[73] Assignee: General Electric Company, Schenectady, N.Y.

[21] Appl. No.: 344,789

[22] Filed: Apr. 28, 1989

[51] Int. Cl.$^4$ ................................................ C07F 7/08
[52] U.S. Cl. .................................................... 556/439
[58] Field of Search ........................................ 556/439

[56] References Cited

U.S. PATENT DOCUMENTS

| | | | |
|---|---|---|---|
| 2,721,856 | 10/1955 | Lomme | 556/439 X |
| 2,957,899 | 10/1960 | Black et al. | 556/439 |
| 3,715,377 | 2/1973 | Siciliano | 556/439 X |
| 4,604,477 | 8/1986 | Rich | 556/439 X |

Primary Examiner—Paul F. Shaver
Attorney, Agent, or Firm—William A. Teoli; James C. Davis, Jr.; William H. Pittman

[57] ABSTRACT

A method is provided for making carboxy aryl terminated organosiloxanes, such as 1,1,3,3-tetramethyl-1-3-disiloxane diyl) bis(benzoic acid) by heating a mixture of an aqueous organic solvent and the corresponding haloacyl aryl terminated organosiloxane. The carboxy aryl terminated organolsiloxanes of the present invention can be used to make silicone polyester block copolymers and silicone polycarbonate block copolymers where the silicone block is joined to the organic block by an ester linkage.

5 Claims, No Drawings

METHOD FOR MAKING CARBOXY ARYL TERMINATED ORGANOSILOXANES

BACKGROUND OF INVENTION

The present invention relates to a method for converting haloacylaryl terminated organosiloxanes to the corresponding carboxyaryl terminated organosiloxanes by employing an aqueous mixture of an organic solvent, such as acetone.

Prior to the present invention, 4,4'-(1,1,3,3-tetramethyl-1,3-disiloxanediyl) bis(benzoic acid) having the formula,

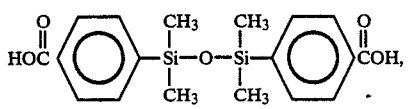
(1)

was made by the transition metal oxidation of the corresponding 1,3 alkylphenyl terminated tetramethyldisiloxane, or the caustic hydrolysis of the corresponding cyanophenyl terminated tetramethyldisiloxane. Tetramethyldisiloxane bis(benzoic acid) of formula (1) can be used in the preparation of a variety of liquid crystalline silicone polyesters as shown in copending application Ser. No. 319,028, filed Mar. 2, 1989.

As shown by Rich, U.S. Pat. No. 4,709,054, which is incorporated herein by reference, the intermediate 2-chlorodimethylsilylbenzoylchloride and 3-chlorodimethylsilylbenzoylchloride can be made by effecting reaction between isophthaloylchloride or terephthaloyl chloride and a chloropolymethylsilane, such as 1,1,2,2-tetradimethyldichlorodisilane in the presence of a transition metal catalyst. Rich by U.S. Pat. Nos. 4,604,442 and 4,604,477, which are incorporated herein by reference, shows that the corresponding tetramethyldisiloxane- bis(benzoyl chloride) can be made by hydrolyzing one of the aforementioned chlorodimethylsilylbenzoylchlorides. However, attempts to hydrolyze the aforementioned tetramethyldisiloxane bis(benzoyl chloride) to produce the corresponding diacid of formula (1) by standard means leads to decomposition of the starting material For example, treatment of tetramethyldisiloxane bis(benzoyl chloride) with either a 2% aqueous sodium hydroxide solution, or saturated sodium bicarbonate solution, results in the production of significant amounts of the corresponding cleavage product of the formula,

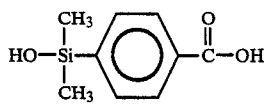

SUMMARY OF THE INVENTION

It would be desirable to prepare carboxyaryl terminated polydiorganosiloxane of formula (1) by a straight forward method which would not involve the oxidation of pendent nuclear bound alkyl radicals, or the caustic hydrolysis of cyanoaryl radicals requiring a multi step procedure. It also would be desirable to provide a straight forward method to effect the conversion of organosiloxane having terminal haloaroyl groups, to the corresponding arylcarboxylic acid terminated organosiloxane without significant cleavage occurring in the organosiloxane chain.

The present invention is based on the discovery that haloacylaryl terminated polydiorganosiloxane having the formula,

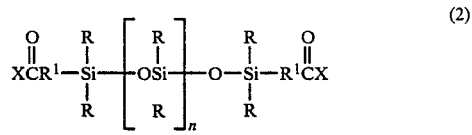
(2)

can be converted to the corresponding diacid such as shown by the disiloxane of formula (1), by heating an aqueous mixture of the haloacylaryl terminated polydiorganosiloxane and an organic solvent at temperatures in the range of from 25° C. to 100° C, or under reflux conditions, where R is selected from the same or different $C_{(1-13)}$ monovalent hydrocarbon radicals and $C_{(1-13)}$ monovalent hydrocarbon radicals substituted with radicals inert during equilibration or condensation, $R^1$ is selected from the same or different divalent $C_{(6-13)}$ aromatic hydrocarbon radicals and divalent $C_{(6-13)}$ aromatic hydrocarbon radicals substituted with radicals inert during equilibration and condensation, n is a whole number equal to 0 to 10 inclusive and X is a halogen radical, and preferably chloro. The haloacylaryl terminated polydiorganosiloxane of formula (2) where n has a value of 1 to 10 can be made by the procedure shown by Rich, U.S. Pat. No. 4,604,477, incorporated herein by reference.

STATEMENT OF THE INVENTION

There is provided by the present invention a method for making carboxyaryl terminated organosiloxanes having the formula,

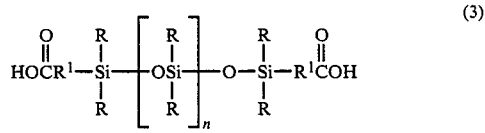
(3)

which comprises, hydrolyzing a haloacyl aryl terminated organosiloxane of formula (2), in the presence of an aqueous organic solvent mixture at a temperature in the range of from 25° C. to 100° C., and (2) recovering the resulting carboxyaryl terminated organosiloxane from the mixture of (1), where R, $R^1$: and n are as previously defined.

Radicals included within R of formulas 1 and 2 are for example $C_{(1-8)}$ alkyl radials, such as methyl, ethyl, propyl, butyl, pentyl, hexyl; alkenyl radicals such as vinyl, propenyl; cycloaliphatic radicals such as cyclophenyl, cyclohexyl, substituted alkyl radicals such as trifluoropropyl, cyanoethyl, cyanopropyl; aryl radicals such phenyl, tolyl, xylyl, naphthyl; substituted aryl radicals such as chlorophenyl, nitrophenyl, cyanophenyl. Radicals included within $R^1$, are for example, the same or different arylene radicals such as phenylene, tolylene, xylylene, naphthylene and substituted arylene radicals, such as halophenylene, nitrophenylene.

In the practice of the invention, the haloacyl aryl terminated polydiorganosiloxane of formula (2) is hydrolyzed in an aqueous inert organic solvent at temperatures in a range from about 25° C. to 100° C. There can be used from about 1% to about 50% by weight of water, based on total weight of aqueous inert organic solvent medium and preferably about 5% to 20% by weight. Suitable organic solvents are water miscible solvents, such as acetone, dioxane, and tetrahydrofuran. It is preferred to effect the hydrolysis of the haloacyl aryl terminated polydiorgano-siloxane under reflux conditions. Recovery of the resulting carboxyaryl terminated polydiorganosiloxane of formula 3 can be achieved by standard procedures, such as filtration, and recrystalization from an organic solvent such as 1,2-dichlorobenzene.

Carboxyaryl terminated polydiorganosiloxanes of the present invention can be used as intermediates in making silicone block copolymers, such as polyester siloxanes or polycarbonate siloxanes, where the silicone block and the organic block are joined by ester or amide linkages. Copolymerization can be achieved under neat conditions in an extruder reactor, since the condensation reaction is free of by-products, such as hydrogen chloride.

In order that those skilled in the art will be better able to practice the present invention, the following example is given by way of illustration and not by way of limitation.

EXAMPLE

A mixture of 110.75 grams (269 mmol) of p,p (1,1,3,3-tetramethyl-1,3-disiloxanediyl)bisbenzoylchloride and 675 ml of a 10% H$_2$O/acetone solution was refluxed for three hours. After cooling to room temperature, the mixture was distilled. After the acetone was removed, the residue was diluted with 800 ml of water. Filtration of the residue, followed by re-crystalization from 1,2-dichlorobenzene provided 81.12 grams, (81%) of 1,1,3,3-tetramethyl-1,3disiloxanediyl) bisbenzoic acid having a melting point of 242°-244° C. It was a white crystalline solid. Its identity was further confirmed by $^1$H NMR (90 MHz, CD$_3$COCD$_3$) δ0.42 (s,12H), 7.82 (d,J=8 Hz, 4H), 8.12 (d,J=8 Hz, 4H).

Although the above example is directed to only a few of the very many variables of which can be used in the practice of the method of the present invention, it should be understood that the present invention is directed to the synthesis of a much broader variety of carboxy aryl terminated polydiorganosiloxanes as shown in the description preceding this example.

What is claimed is:

1. A method for making carboxy aryl terminated organosiloxanes having the formula,

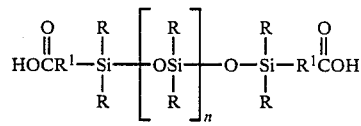

which comprises, (1) hydrolyzing a haloacyl aryl terminated organosiloxane of the formula,

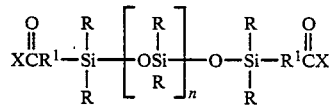

in the presence of an aqueous insert organic solvent mixture at a temperature in the range of from 25° C. to 100° C., and, (2) recovering the resulting carboxyaryl terminated organosiloxane from the mixture of (1), where R is selected from the same or different C$_{(1-13)}$ monovalent hydrocarbon radicals and C$_{(1-13)}$ monovalent hydrocarbon radicals substituted with radicals inert during equilibration or condensation, R$^1$ is selected from the same or different divalent C$_{(6-13)}$ aromatic hydrocarbon radicals and divalent C$_{(6-13)}$ aromatic hydrocarbon radicals substituted with radicals inert during equilibration and condensation, n is a whole number equal to 0 to 10 inclusive and X is a halogen radical.

2. A method in accordance with claim 1, where the haloacylaryl terminated organosiloxane is the diacid chloride of the p,p (1,1,3,3-tetramethyl-1,3-disiloxanediyl)bisbenzoic.

3. A method in accordance with claim 1, where the organic solvent is acetone.

4. A method in accordance with claim 1, where there is used 5% to 20% by weight water with the aqueous inert organic solvent.

5. A method in accordance with claim 1 where the hydrolysis is effected under reflux conditions.

* * * * *